US 8,387,895 B2

(12) United States Patent
Stangl

(10) Patent No.: US 8,387,895 B2
(45) Date of Patent: Mar. 5, 2013

(54) INHALATION NEBULIZER

(75) Inventor: Roland Stangl, Moosburg (DE)

(73) Assignee: PARI Pharma GmbH, Starnberg (DE)

( * ) Notice: Subject to any disclaimer, the term of this patent is extended or adjusted under 35 U.S.C. 154(b) by 1134 days.

(21) Appl. No.: 11/998,830

(22) Filed: Nov. 30, 2007

(65) Prior Publication Data

US 2008/0299049 A1     Dec. 4, 2008

(30) Foreign Application Priority Data

Nov. 30, 2006   (EP) ..................................... 06024796

(51) Int. Cl.
*B05B 1/08*      (2006.01)
*A61M 11/00*     (2006.01)
*A61M 11/06*     (2006.01)

(52) U.S. Cl. ................ 239/102.2; 239/338; 128/200.14; 128/200.16

(58) Field of Classification Search ............... 239/102.2, 239/338; 128/200.14, 200.16
See application file for complete search history.

(56) References Cited

U.S. PATENT DOCUMENTS

| | | | | | |
|---|---|---|---|---|---|
| 5,152,456 | A | * | 10/1992 | Ross et al. | 239/102.2 |
| 5,261,601 | A | * | 11/1993 | Ross et al. | 239/102.2 |
| 5,518,179 | A | * | 5/1996 | Humberstone et al. | 239/102.2 |
| 6,962,151 | B1 | * | 11/2005 | Knoch et al. | 128/200.14 |
| 6,983,747 | B2 | * | 1/2006 | Gallem et al. | 128/203.12 |

FOREIGN PATENT DOCUMENTS

| | | |
|---|---|---|
| EP | 1 142 600 A1 | 10/2001 |
| WO | WO 01/34232 A1 | 5/2001 |
| WO | WO 2004/052436 A1 | 6/2004 |

OTHER PUBLICATIONS

The TRIO® electronic nebulizer instructions for use (accessed on Aug. 15, 2011 at http://www.sourcecf.com/eflow.htm.*
Wilkens et al., "Breathing pattern and chest wall volumes during exercise in patients with cystic fibrosis, pulmonary fibrosis, and COPD before and after lung transplantation," Thorax Sep. 2010, 65(9), pp. 808-814.*
Shawn Thistle, "Altered Breathing Patterns in Chronic Low Back Pain Patients," Dynamic Chiropractic, Jul. 1, 2011, vol. 29, Issue 14, accessed on Mar. 3, 2012 at www,dynamicchiropractic.com/mpacms/dc/article.php?id=55405.*
D.C.J. Howell, "Breathing Patterns" In Signs of Respiratory Disease, Elsevier, Ltd.: New York, 2006, pp. 18-22.*
Search report dated Apr. 27, 2007 from European Application No. EP 06024796.

* cited by examiner

*Primary Examiner* — James H. Alstrum-Acevedo
(74) *Attorney, Agent, or Firm* — Wolf, Greenfield & Sacks, P.C.

(57) ABSTRACT

The aerosol generator of an inhalation therapy device according to a preferred embodiment of the invention continuously produces an aerosol at a generation rate of about 0.2 ml/min to about 1.5 ml/min, preferably 0.4 ml/min to about 1.2 ml/min and the mixing chamber has a volume of about 60 ml to about 150 ml, preferably about 80 ml to about 120 ml, and even more preferably about 90 to about 110 ml. While the patient inhales through the inhalation therapy device, the generated aerosol is inhaled by the patient. While the patient exhales into the inhalation therapy device, the generated aerosol is collected in the mixing chamber. Due to the specific size of the mixing chamber, the continuously generated aerosol can accumulate therein without losses even when the exhalation phase is longer than the inhalation phase like in the case of emphysema.

17 Claims, 2 Drawing Sheets

INHALATION NEBULIZER

Figure 1:
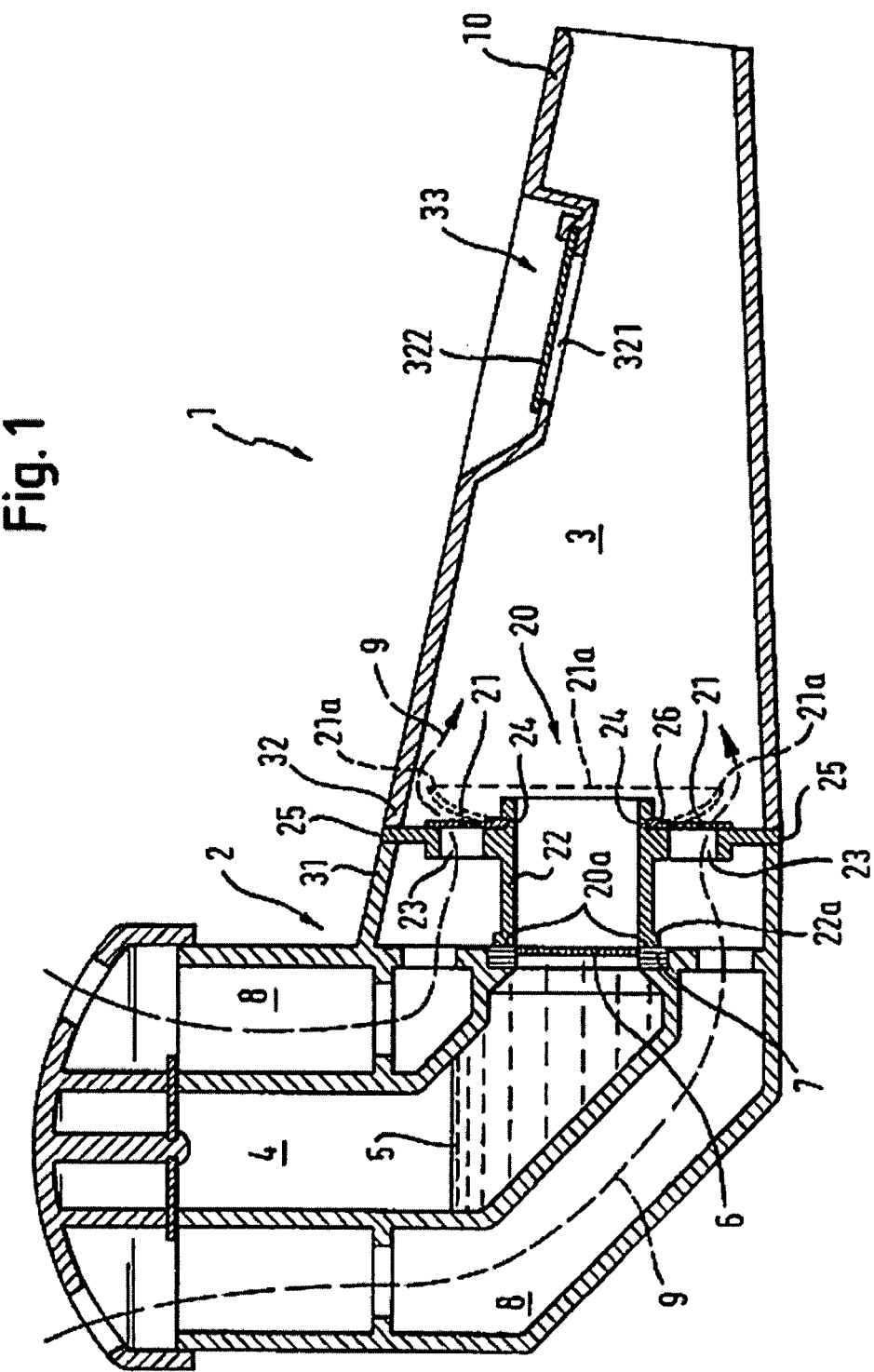

The invention relates generally to inhalation therapy devices having an aerosol generator for generating an aerosol of a liquid drug or a liquid that contain a drug. More specifically, the invention relates to inhalation therapy devices adapted to disease specific breathing patterns.

Inhalation therapy devices deliver therapeutically effective amounts of drugs by forming an aerosol comprising particles of a size, typically μm 0.5 to 6 μm, that can be inhaled such that the therapeutically effective drug or pharmaceutical reaches intended areas of the patient's respiratory tract upon inhalation.

WO 01/34232 relates to a nebulizer that comprises a liquid storage container for a liquid medicament, an aerosol generator and a mixing chamber. The aerosol generator includes a diaphragm that is connected on one side to the liquid storage container such that a liquid contained in the liquid storage container will come into contact with one side of the diaphragm. The diaphragm is attached to a vibration generator that can vibrate the diaphragm so that a liquid in the liquid storage container can be dispensed or dosed for atomization through openings present in the diaphragm. The aerosol generated upon vibrating the diaphragm enters the mixing chamber.

The mixing chamber has an inhalation valve that allows ambient air to flow into the mixing chamber during an inhalation phase while preventing aerosol from escaping during an exhalation phase. The mixing chamber or a mouthpiece attached to it has an exhalation valve that allows discharge of the patient's respiratory air during the exhalation phase while preventing an inflow of ambient air during the inhalation phase.

While the above nebulizer is very effective and allows administering a precise dose of the drug, the present invention provides an improved inhalation therapy device by taking into consideration that some chronic lung diseases are associated with specific breathing patterns.

The natural breathing pattern may be significantly impaired in patients suffering from severe pulmonary diseases such as asthma, COPD, bronchiectasis, lung infections, pulmonary and cystic fibrosis, sarcoidosis, bronchiolitis obliterans, hormone or enzyme or neurotransmitter deficiency, pulmonary hypertension and other parenchymatic or non parchenchymatic diseases affecting uptake and exchange of air in the lungs.

For example, lung emphysema is known as one indication occurring in late stages of COPD, e.g. in patients suffering from alpha 1-antitrypsin deficiency (A1AD). Inhaled treatment of patients with an emphysematic breathing pattern with aerosolized alpha 1-antitrypsin (A1AT) is used as an example demonstrating the improvement when the inventive inhalation system is used.

Emphysema is often caused by exposure to toxic chemicals or long-term exposure to tobacco smoke. It is characterized by loss of elasticity of the lung tissue, destruction of structures supporting the alveoli, and destruction of capillaries feeding the alveoli. The result is that the small airways collapse during expiration, leading to an obstructive form of lung disease. Air is trapped in the lungs in such obstructive lung diseases.

Emphysema occurs in a higher proportion in patients with decreased levels of A1AT, i.e. A1AD. In A1AD, inflammatory enzymes, such as elastase, are able to destroy the alveolar tissue, for example the elastin fibre. Most A1AD patients do not develop clinically significant emphysema, but smoking and severely decreased A1AT levels (10-15%) can cause emphysema already at a young age.

Current augmentation therapy consists of intravenous AAT application in doses of about 60-90 mg/kg body weight (about 4-7 g total dose) given once weekly. This treatment regime is burdensome, lasts about 1 hour and only about 2% of the dose is estimated to reach the target tissue of the lungs.

Specifically applicable drug classes in the context of the above diseases are antibiotics, antifungals, immunmodulators, beta-agonists, cytostatic drugs, steroids, xanthines, non-steroidal anti-inflammatory drugs, mucolytics, proteins, peptides, genes or other drug compounds or medications suitable for treating pulmonary diseases. Drug compounds falling within such classes may be formulated as solid (lyophylisates, powders) or liquid drug products, such as solutions, suspensions, emulsions, colloidal systems or liposomes, all for administration as liquid aerosols.

The present invention takes special account of the fact that in the above mentioned cases patients show a specific breathing pattern that consists of a relatively short inhalation phase followed by a prolonged exhalation phase. Parameters of a typical breathing pattern are: tidal volume 450 ml, 17 breaths per minute and an inspiration/expiration ratio (I/E ration) of 1:2 to 1:3.

To provide an improvement with respect to the breathing pattern, an inhalation therapy device according to the invention comprises a liquid storage container into which a liquid can be filled; an aerosol generator comprising a diaphragm which is arranged with respect to the liquid storage container such that a liquid filled into the liquid storage container comes into contact with one side of the diaphragm; and a vibration generator capable of causing the diaphragm to vibrate such that a liquid filled into the liquid storage container is nebulized and expelled as an aerosol on the other side of the diaphragm through openings of the diaphragm at an aerosol generation rate in the range of about 0.2 ml/min to about 1.5 ml/min, preferably about 0.4 ml/min to about 1.2 ml/min; a mixing chamber into which the aerosol generator delivers the aerosol and which has a volume in the range of about 60 ml to about 150 ml, preferably about 80 ml to about 120 ml, and even more preferably about 90 to about 110 ml; an inhalation valve that is open to allow an inflow of ambient air into the mixing chamber during an inhalation phase and is closed to prevent escape of the aerosol from the mixing chamber during an exhalation phase; and an exhalation valve that is open to allow the discharge of the respiratory air of a patient into the surroundings during the exhalation phase and is closed to prevent the inflow of ambient air during the inhalation phase.

According to a preferred embodiment of the invention, the aerosol generator continuously produces an aerosol at a generation rate of about 0.2 ml/min to about 1.5 ml/min, preferably about 0.4 ml/min to about 1.2 ml/min while the mixing chamber has a volume of about 60 ml to about 150 ml, preferably about 80 ml to about 120 ml, and even more preferably about 90 to about 110 ml. While the patient inhales through the inhalation therapy device, the generated aerosol is inhaled by the patient. While the patient exhales into the inhalation therapy device, the generated aerosol is collected in the mixing chamber. Due to the specific size of the mixing chamber, the continuously generated aerosol can accumulate therein without losses even when the exhalation phase is longer than the inhalation phase like in the case of emphysema.

The aerosol generator may comprise a perforated membrane, diaphragm or mesh where pressure fluctuations within the liquid supplied to one side of the membrane cause the liquid to be ejected through the perforations to form regularly sized aerosol droplets emerging from the other side of the membrane. The pressure fluctuations may either be generated by vibration of the membrane itself or by an actuator located adjacent to the membrane and being in direct or indirect contact with the bulk liquid in the liquid storage container.

Since aerosol is accumulated in the mixing chamber during exhalation as a fine respirable aerosol cloud, not only the amount of aerosol generated due to the continuous production is available for the inhalation, but at the beginning of the inhalation phase an aerosol bolus can be inhaled, which is available because of aerosol accumulation during the exhalation phase.

Here the invention takes advantage of the special characteristics of the atomization of a liquid by an aerosol generator comprising a diaphragm, in particular of the comparatively low speed, low ballistic momentum and good respirability of the aerosol particles directly after generation.

In a preferred embodiment, the aerosol generator comprising a diaphragm is adapted to generate an aerosol having a mass median aerodynamic diameter (MMAD) that ranges from about 1 μm to about 6 μm. This can be achieved by defining openings in the diaphragm by providing the openings with a suitable diameter and shape.

In a preferred embodiment, the diaphragm forms a part of the wall of the liquid storage container so that a liquid within the liquid storage container directly contacts the diaphragm, thereby ensuring continuous aerosol generation.

Preferably, the vibration generator is a piezoelectric element in the form of a circular piezo-electric disk attached to a circular ring disk supporting the diaphragm.

Further features and advantages of the invention will become apparent from the following description of a preferred embodiment of the invention and of the results achieved with an improved inhalation therapy device according to the invention.

The inhalation therapy device according to the invention may be equally beneficial for the systemic delivery of drug compounds via the pulmonary route. With perforated membrane nebulizers, storage of a high density aerosol cloud in a large volume mixing chamber optimized for a distinct aerosol generation rate will significantly increase the amount of aerosolized drug inhaled with each breath while minimizing aerosol losses caused by sedimentation and impaction in the mixing chamber as well as by escaping to the surroundings. Drug classes potentially suitable for systemic delivery via the lungs are any drugs and molecules used for the treatment of human diseases and favourably administered via the pulmonary route in case of degradation, poor bioavailability or high systemic side effects following oral application. Drugs among these classes are genes, small and large molecule proteins and peptides, pain-killers, hormones, opiates, anti cancer drugs, canabinoids, etc.

Figure 2:
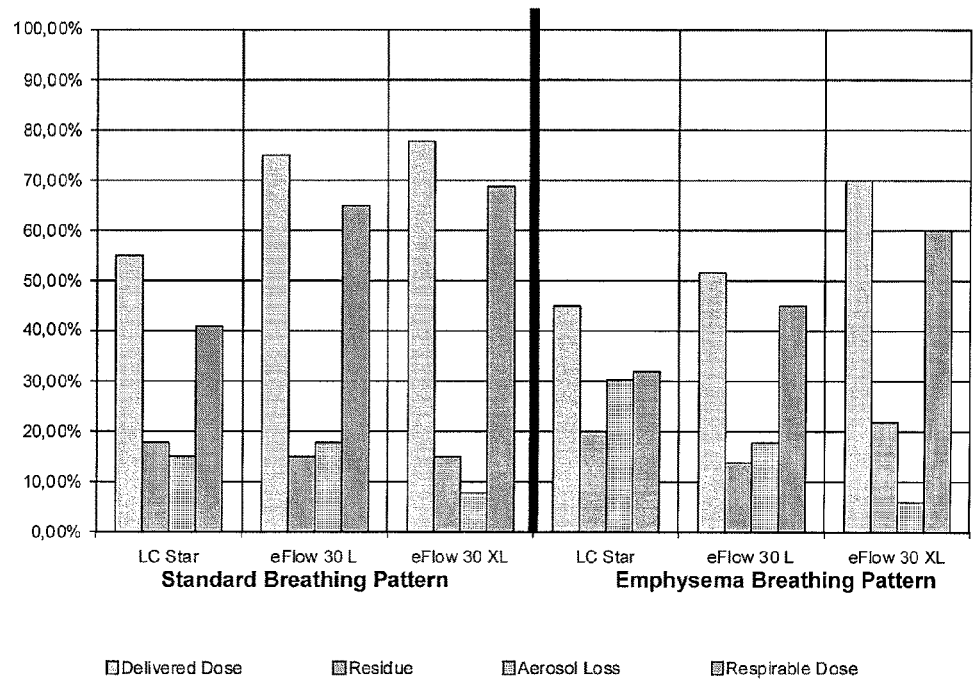
Figure 3:
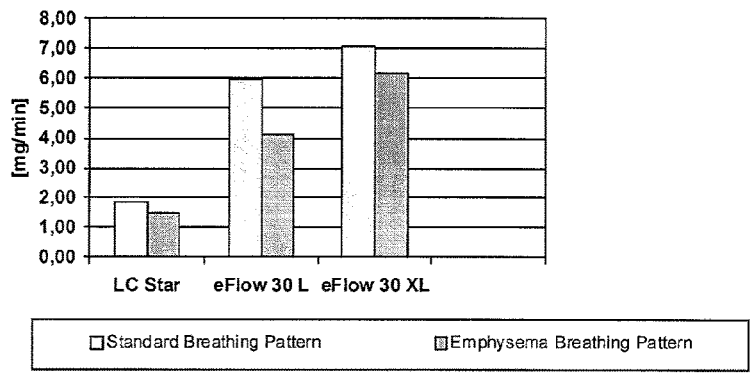

In the following a preferred embodiment of the invention will be described with reference to the drawing in which FIG. 1 shows a sectional view of an embodiment of an inhalation therapy device according to the invention;

FIG. 2 shows results of measurements regarding some performance aspects of an inhalation device according to the invention; and FIG. 3 shows results of measurements regarding some other performance aspects of an inhalation device according to the invention.

FIG. 1 shows an embodiment of an inhalation therapy device 1 according to the invention, comprising an aerosol membrane generator 2 and a mixing chamber 3. In the shown embodiment, the two components are configured as separate units that are connected with one another in a suitable manner such that both components can be safely handled together as a functional unit.

The aerosol generator 2 of the embodiment according to FIG. 1 is attached to a liquid storage container 4, into which a medicament-containing liquid 5 can be filled, and a diaphragm or membrane 6 which closes the liquid storage container 4 at an open surface. The membrane 6 is thereby connected on one side with the liquid container 4 such that the liquid 5 disposed in the liquid storage container contacts the one side of the membrane 6. A vibration generator 7, for example a piezoelectric element, is arranged with respect to the membrane 6 such that the membrane 6 is caused to oscillate when the vibration generator 7 is activated. In the embodiment shown here, the membrane 6 and the vibration generator 7 are configured in a rotationally symmetrical manner such that the vibration generator 7 concentrically surrounds the membrane. In such an embodiment, the aerosol generator preferably comprises a ring-shaped disk which is arranged to support the membrane and to which a ring-shaped piezo-electric disk is attached concentrically.

If the vibration generator 7 is activated, i.e., for example, if an alternating voltage is supplied to the piezoelectric element, the membrane 6 is caused to oscillate such that the liquid 5 that is disposed in the liquid storage container and contacts the membrane 6 is guided through openings in the membrane to the other side of said membrane 6 and is nebulized there into an aerosol. The aerosol is released into the mixing chamber 3.

According to the invention, the vibration generator is capable of causing the membrane to vibrate such that aerosol is generated at an aerosol generation rate (AGR) in the range of about 0.2 ml/min to about 1.5 ml/min, preferably about 0.4 ml/min to about 1.2 ml/min. Further, the mixing chamber into which the aerosol generator delivers the aerosol has a volume in the range of about 60 ml to about 150 ml, preferably about 80 ml to about 120 ml, and even more preferably about 90 to about 110 ml.

In a preferred embodiment, the aerosol generator is adapted to produce an aerosol having a mass median aerodynamic diameter (MMAD) that ranges from about 1 μm to about 6 μm.

The embodiment shown in FIG. 1 is furthermore provided with a mouthpiece 10 which is configured integrally with the mixing chamber 3 in the shown example, but which, however, can also be formed so as to be separable from the mixing chamber 3 in a modified embodiment. The patient inhales the aerosol that is generated by the aerosol membrane generator 2 and released into the mixing chamber 3 via the mouthpiece 10 when he breathes in through said mouthpiece.

During the inhalation phase, ambient air flows into the therapy device via air supply channels 8 that are formed in the aerosol membrane generator 2, and reaches the mixing chamber 3; the flow path of the supplied air is indicated in FIG. 1 by the dashed arrow lines 9. A valve element 21, which is described in more detail below, is thereby raised, which corresponds to the dashed position 21a in FIG. 1.

According to the invention, an inhalation valve 20 is provided to control the supplied air, which allows ambient air to flow into the mixing chamber during the inhalation phases but which, however, prevents exhaled air from entering the mixing chamber and reversely passing the aerosol generator 2 in exhalation phases. The inhalation valve 20 according to the invention therefore prevents the aerosol being transported out of the mixing chamber with the exhaled air in exhalation phases and prevents exhaled air from flowing into the aerosol membrane generator 2. In the aerosol generator 2, the area around the liquid container 4, in which other components, for example electrical connections for activating the piezo crystal, can often also be found, is thereby protected from exhaled air and thus from impurities which could enter the therapy device with the exhaled air. The inhalation valve 20 therefore protects the interior of the aerosol generator 2 during the exhalation phases by closing the mixing chamber 3 towards the aerosol membrane generator 2.

The exhaled air is guided away from the mixing chamber 3 in another manner, for example via a mouthpiece valve 32, which comprises a mouthpiece valve opening 321 and a mouthpiece valve element 322. When a patient exhales into the opening of the mouthpiece 10, the exhalation valve 32 is opened so that the exhaled air of the patient is discharged into the surroundings. To this end, a valve element 322 of the exhalation valve 32 is lifted and frees the opening 321 of the exhalation valve 32. The inhalation valve is closed when the patient exhales into the inhalation therapy device, as the valve element of the inhalation valve closes the openings of said valve.

As aerosol has accumulated in the mixing chamber 3 during an exhalation phase, there is available to the patient an increased amount of aerosol, a so-called aerosol bolus, especially at the beginning of an inhalation phase.

Different configurations of an inhalation therapy device according to the present invention were used to nebulize a highly purified 2% human, liquid, ready-to-use AAT preparation (Kamada Ltd, Rehovot, Israel). The results were compared with a jet nebulizer.

Geometric aerosol droplet size distribution was determined by laser diffraction (LD) utilizing a Malvern MasterSizerX (Malvern, Herrenberg, Germany).

Aerosol delivery efficiency was determined by breath simulation using the emphysema breathing pattern (tidal volume=450 ml, 17 breaths per minute and an inspiration/expiration ratio of 1:2.5) generated by a breath simulator. As a reference, a standardized human breathing pattern (tidal volume=500 ml, 15 breaths/min, inspiration/expiration ratio of 1:1) was also investigated. Samples were analysed for protein content by UV analysis at 280 nm with a photometer CARY 50 (Varian GmbH, Darmstadt, Germany).

Nebulization time was determined by an electronic shut-off of the piezoelectric aerosol generator upon nebulization of the entire content of the medication storage container. The drug being left in the device corresponds to the drug residue.

The in-vitro delivered dose (DD) corresponds to drug collected and assayed from inspiratory filters and aerosol losses from exhalation filters.

The in-vitro respirable dose (RD) was calculated by multiplying the delivered dose (DD) by the % respirable fraction (RF=droplets<5 µm) obtained form LD data.

The Respirable Drug Delivery Rate (RDDR) is determined by dividing the RD (in mg) by the treatment time.

The Alpha-1-Antitrypsin (A1AT) activity of two different formulation lots was investigated pre and post nebulization. The results of the A1AT activity test showed that 90.0% of the specific activity of the first lot and 94.5% specific activity of the second lot were retained. There is no increase in the amount of dimers or oligomers and no formation of aggregates.

| Droplet Size Distribution | MMAD | GSD | Respirable Fraction |
|---|---|---|---|
| State-of-the art jet nebulizer (LC Star) | 3.5 µm | 1.9 | 73.0% |
| Therapy device 1 according to the invention (eFlow 30 L; 48 ml mixing chamber; AGR 0.4 ml/min) | 3.1 µm | 1.5 | 87.9% |
| Therapy device 2 according to the invention (eFlow 30 XL; 95 ml mixing chamber; AGR 0.4 ml/min) | 3.1 µm | 1.5 | 87.9% |

Consistently the inhalation therapy device according to the invention showed the best delivered dose result for the disease specific breathing pattern (eFlow 30 XL: 69±7%), while a known inhalation therapy device comprising a membrane aerosol generator showed already good results (eFlow 30 L: 52±1%) compared to a jet nebulizer which showed a lower delivered dose (LC Star: 45±4%). It is noticeable, that the inhalation therapy device according to the invention shows constant and very low aerosol losses (6±1%). The respirable dose (RD) shows similar improvements of the results for the inhalation therapy device according to the invention (eFlow 30 XL: 60.7%) compared to the known inhalation therapy device comprising a membrane aerosol generator (eFlow 30 L: 45.7%) and due to the high respirable fraction even higher improvements of the results compared to the jet nebulizer (LC Star: 32.9%). The above and further results can be taken from FIG. 2.

The treatment times were determined as follows: jet nebulizer (LC Star) 20.0 min, the known therapy device (eFlow 30 L) 10.1 min, and the therapy device according to the invention (eFlow 30 XL) 9.0 min. Determining the RDDR using the respirable dose, the drug concentration and the treatment time shows that the therapy device according to the invention (eFlow 30 XL) delivers 6.20 [mg/min], the known therapy device (eFlow 30 L) 4.15 [mg/min] and the jet nebulizer (LC Star) 1.51 [mg/min]. The above and other results can be taken from FIG. 3.

In order to estimate the number of different patients that can be treated with a limited drug resource such as A1AT, a dose factor can be introduced. With the same amount of drug one can treat 1.85 times the number of patients when using the therapy device according to the invention instead of a jet nebulizer in case of a lung disease with a specific breathing pattern such as A1AD.

In summary, use of an inhalation therapy device according to the invention for inhaling specific drugs mentioned above, for example A1AT, leads to a significantly faster and drug saving inhalation therapy.

The invention claimed is:
1. An inhalation therapy device comprising:
a liquid storage container into which a liquid can be filled;
an aerosol generator comprising:
    a membrane which is arranged with respect to the liquid storage container such that a liquid filled into the liquid storage container comes into contact with one side of the membrane; and a vibration generator capable of causing the membrane to vibrate such that a liquid filled into the liquid storage container is nebulized and expelled as an aerosol on the other side of the membrane through openings of the membrane at an aerosol generation rate in the range of about 0.2 ml/min to about 1.5 ml/min;

a mixing chamber into which the aerosol generator delivers the aerosol and which has a volume in the range of about 60 ml to about 150 ml;

an inhalation valve that is open to allow an inflow of ambient air into the mixing chamber during an inhalation phase and is closed to prevent escape of the aerosol from the mixing chamber during an exhalation phase; and an exhalation valve that is open to allow the discharge of the respiratory air of a patient into the surroundings during the exhalation phase and is closed to prevent the inflow of ambient air during the inhalation phase.

2. The inhalation therapy device of claim 1, wherein the aerosol generator is adapted to produce an aerosol having a mass median aerodynamic diameter (MMAD) that ranges from about 1 μm to about 6 μm.

3. The inhalation therapy device of claim 1, wherein the membrane forms a part of the wall of the liquid storage container and partially defines the liquid storage container such that a liquid filled into the liquid storage container directly contacts the membrane.

4. The inhalation therapy device of claim 1, wherein the aerosol generator comprises a ring-shaped disk which is arranged to support the membrane and to which a ring-shaped piezo-electric disk is attached concentrically.

5. The inhalation therapy device of claim 1, wherein the exhalation valve is arranged at a mouthpiece which is removably mounted at the mixing chamber and through which the patient inhales the aerosol from the mixing chamber.

6. The inhalation therapy device of claim 1, wherein the exhalation valve is arranged in a wall of the mixing chamber.

7. The inhalation therapy device of claim 1, wherein the liquid consists of or contains a drug effective against a pulmonary disease selected from the group consisting of asthma, chronic obstructive pulmonary disease (COPD), bronchiectasis, lung infections, pulmonary and cystic fibrosis, sarcoidosis, bronchiolitis obliterans, hormone or enzyme or neurotransmitter deficiency, and pulmonary hypertension.

8. The inhalation therapy device of claim 7, wherein the drug consists of or comprises alpha one anti-tripsin (A1AT).

9. The inhalation therapy device of claim 1, wherein the liquid consists of or contains any drug out of the following drug classes: antibiotics, antifungals, immunmodulators, beta-agonists, cytostatic drugs, steroids, xanthines, non-steroidal anti-inflammatory drugs, mucolytics, proteins, peptides, or genes.

10. The inhalation therapy device of claim 9, wherein the drug may be formulated as solid (lyophylisates, powders) or liquid drug products selected from the group consisting of solutions, suspensions, emulsions, colloidal systems or liposomes, all for administration as liquid aerosols.

11. The inhalation therapy device of claim 1, wherein the liquid consists of or contains any drug out of the following drug classes: genes, proteins, peptides, pain-killers, hormones, opiates, anti cancer drugs, or canabinoids.

12. The inhalation therapy device of claim 1, wherein the vibration generator is capable of causing the membrane to vibrate such that a liquid filled into the liquid storage container is nebulized and expelled as an aerosol on the other side of the membrane through openings of the membrane at an aerosol generation rate in the range of about 0.4 ml/min to about 1.2 ml/min.

13. The inhalation therapy device of claim 1, wherein the mixing chamber has a volume in the range of about 80 ml to about 120 ml.

14. The inhalation therapy device of claim 1, wherein the mixing chamber has a volume in the range of about 90 ml to about 110 ml.

15. The inhalation therapy device of claim 1, wherein at the beginning of the inhalation phase an aerosol bolus in the mixing chamber is available to the patient.

16. The inhalation therapy device of claim 1, wherein the device is suitable for treating pulmonary diseases with drug compounds or medications.

17. The inhalation therapy device of claim 1, wherein the device is suitable for systemic delivery via the lungs of drug compounds or medications.

* * * * *

UNITED STATES PATENT AND TRADEMARK OFFICE
CERTIFICATE OF CORRECTION

| | | |
|---|---|---|
| PATENT NO. | : 8,387,895 B2 | Page 1 of 1 |
| APPLICATION NO. | : 11/998830 | |
| DATED | : March 5, 2013 | |
| INVENTOR(S) | : Roland Stangl | |

It is certified that error appears in the above-identified patent and that said Letters Patent is hereby corrected as shown below:

In the Claims:

At column 7, claim 1, line 8 should read as follows:

the aerosol and which has a volume in the range of

Signed and Sealed this
Twenty-third Day of April, 2013

Teresa Stanek Rea
*Acting Director of the United States Patent and Trademark Office*